(12) United States Patent
Pagani et al.

(10) Patent No.: US 8,967,000 B2
(45) Date of Patent: Mar. 3, 2015

(54) PLANAR ELECTRIC BOARD WITH PLIABLE WINGS AND SYSTEM FOR SENSING COMPONENTS ALONG THREE COORDINATE AXIS OF INNER FORCES IN A BLOCK MADE OF A BUILDING MATERIAL

(71) Applicant: STMicroelectronics S.r.l., Agrate Brianza (IT)

(72) Inventors: Alberto Pagani, Nova Milanese (IT); Federico Giovanni Ziglioli, Pozzo d'Adda (IT)

(73) Assignee: STMicroelectronics S.r.l., Agrate Brianza (MB) (IT)

( * ) Notice: Subject to any disclaimer, the term of this patent is extended or adjusted under 35 U.S.C. 154(b) by 0 days.

(21) Appl. No.: 14/027,990

(22) Filed: Sep. 16, 2013

(65) Prior Publication Data
US 2014/0083206 A1 Mar. 27, 2014

(30) Foreign Application Priority Data
Sep. 25, 2012 (IT) .............................. MI2012A1591

(51) Int. Cl.
*G01L 1/00* (2006.01)
*H05K 1/02* (2006.01)

(52) U.S. Cl.
CPC .............. *G01L 1/005* (2013.01); *H05K 1/0278* (2013.01)
USPC ..................................................... 73/862.68

(58) Field of Classification Search
USPC ..................................................... 73/862.68
See application file for complete search history.

(56) References Cited

U.S. PATENT DOCUMENTS

| | | | |
|---|---|---|---|
| 4,742,183 A * | 5/1988 | Soloway et al. ............... | 174/254 |
| 5,008,496 A | 4/1991 | Schmidt et al. | |
| 5,717,556 A * | 2/1998 | Yanagida ....................... | 361/803 |
| 6,908,583 B2 * | 6/2005 | Fiedler et al. .................. | 264/319 |
| 6,927,344 B1 * | 8/2005 | Gall et al. ...................... | 174/254 |
| 7,265,719 B1 * | 9/2007 | Moosbrugger et al. ...................... | 343/700 MS |
| 8,506,339 B2 * | 8/2013 | Fletcher ............................ | 441/1 |
| 2003/0070483 A1 | 4/2003 | Mueller | |
| 2006/0027395 A1 * | 2/2006 | Cho ................................ | 174/254 |
| 2009/0033467 A1 | 2/2009 | Finocchiaro et al. | |

FOREIGN PATENT DOCUMENTS

WO 2012084295 6/2012

OTHER PUBLICATIONS

Finocchiaro et al., "A 9000-MHz RFID System with TAG-Antenna Magnetically-Coupled to the Die", IEEE Radio Frequency Integrated Circuits Symposium, 2008, pp. 281-284.

* cited by examiner

*Primary Examiner* — Lisa Caputo
*Assistant Examiner* — Octavia Hollington
(74) *Attorney, Agent, or Firm* — Allen, Dyer, Doppelt, Milbrath & Gilchrist, P.A.

(57) ABSTRACT

A planar electric circuit board may include a planar support of a foldable material defining a base surface and wings coupled to the base surface along respective folding lines so that the wings, when folded along the folding lines, are erected with respect to the base surface and remain in that position. An auxiliary circuit is on the planar support and may include pairs of capacitive coupling plates defined on the wings and on the base surface, and electric communication lines coupled to corresponding ones of the pairs of capacitive coupling plates.

23 Claims, 15 Drawing Sheets

PLANAR ELECTRIC BOARD WITH PLIABLE WINGS AND SYSTEM FOR SENSING COMPONENTS ALONG THREE COORDINATE AXIS OF INNER FORCES IN A BLOCK MADE OF A BUILDING MATERIAL

FIELD OF THE INVENTION

This invention relates to monitoring devices in building structures, and, more particularly, to a planar electric board with foldable wings adapted to be used for a system such as for sensing components along three coordinate axis of internal pressure in a block made of building material.

BACKGROUND OF THE INVENTION

The strategy for implementing damage detection and characterization of mechanical structures is commonly called Structural Health Monitoring (SHM). Damage is defined as modifications of the material and/or of the geometrical properties of a structural system, comprising modifications of boundary conditions and connections of the system, that worsen performance of the system. The SHM process implies the observation of the mechanical system during the time using periodically: measurement of dynamic responses coming from an array of sensors, extraction of data of damage characteristics sensed from these measurements, and statistical analysis of these data of characteristics for determining the present health state of the system (also called structural analysis).

This process provides information about the capacity of the structure for carrying out its function, considering the unavoidable aging and degradation in working environments. After extreme events, such as earthquakes or explosions, the SHM is used for a quick screening of the conditions of the structure for providing, almost in real time, reliable information about the integrity of the structure itself.

Nowadays, SHM systems use sensors placed on the surfaces to be controlled. For example, sensors used (anemometers for calculating the wind speed, accelerometers, extensometers, motion transducers, temperature sensors, sensors for detecting motion of weights, etc.) for monitoring bridges are placed on the external surfaces of beams, wire ropes or pillars, in order to: estimate the effects of loads on the bridge, evaluate the weakening of the bridge, and/or foresee the probable evolution of the bridge and its expected lifetime.

SHM systems with sensors adapted to be buried in building structures to be monitored have been devised. These sensing devices include sensors (of pressure, humidity, temperature, etc.) that have at least one remote powering and transmission antenna for transmitting the measured values outside of the block of building material, as in RFID devices (that are sensorless) illustrated in the article by A. Finocchiaro, G. Ferla, G. Girlando, F. Carrara e G. Palmisano, "A 900-MHz RFID System with TAG-Antenna Magnetically-Coupled to the Die", 2008 IEEE Radio Frequency Integrated Circuits Symposium, pages 281-284. This kind of sensing devices are disclosed, for example, in US patent application No. 2009/0033467 and in PCT WO 2012/084295, herein incorporated by reference, and are depicted in FIGS. 1, 2, 3 and 4.

As shown in FIG. 3, the sensor 10 is integrated in a chip IC 1 made of a semiconductor material, is supplied and communicates in a contactless fashion because it is electromagnetically coupled (for example, inductively, or capacitively or through an antenna) with an electric communication line with the outside, as shown in FIGS. 1 and 2. With this technique, sensors buried in the building material may be supplied from the outside and remain galvanically isolated from the respective communication lines with the outside.

Sensing device having sensors electromagnetically coupled to respective communication lines 2, eventually ending with an antenna 22 and equipped with elements of electromagnetic expansion, are shown in FIGS. 3 and 4. Their structure and how they are used is described in detail in PCT application WO 2012/084295. They may be tied to a support 211 buried in a block of building material for sensing at least one characteristic of the building material along the whole block or at least in a portion thereof.

In larger building structures, such as, for example, in pillars of bridges, it may be important to sense the distribution of forces in the structure. To this end, the devices disclosed in the documents US 2009/0033467 and/or WO 2012/084295 are buried inside the structure to remain oriented along three coordinate reference axis, for measuring the three orthogonal components (or in any case according to three different axis) of the forces in the structure.

These pressure sensors are typically provided by an integrated semiconductor circuit with a sensing surface, eventually passivated to be adapted to be placed in direct contact with the building material, that senses a pressure value in a direction orthogonal thereto.

SUMMARY OF THE INVENTION

Tests executed by the applicant showed that during pouring and/or the consequent curing phase of the building material, it may be difficult to keep the desired mutual orientation of the cited sensing devices. This may cause relevant errors in the determination of the distribution of components of the inner forces in a block of building material.

Installing sensing devices of the type disclosed in the cited prior documents on pre-formed rigid three-dimensional structures, that establish the mutual orientation of the devices, would make complex and economically less convenient the mutual positioning of the devices.

In order to address these drawbacks, there is provided a planar electric circuit board with foldable wings along folding lines defined on a base surface to define oriented planes, having an auxiliary circuit comprising pairs of capacitive coupling plates, destined to be electromagnetically coupled to corresponding antennas for contactless power supplying and for transceiving data of sensing devices, and at least two common communication lines to which the corresponding capacitive coupling plates are connected.

This electric circuit board may be used for realizing sensing systems of the inner pressure in a block of building material, and, more generally, for realizing sensing systems of components along three coordinate axis of any physical vector characteristic, by bonding, on the foldable wings and on the base surface, sensing devices having directional sensors of this physical amount or characteristic.

According to an embodiment, the planar electric board comprises a planar support made of material that may be hot and/or cold foldable, wherein the auxiliary circuit is placed on this support. This support may be, for example, in the form of an engraved ribbon of Teflon or of any other thermoplastic material with a plurality of wings, adapted to be hot and/or cold folded to assume a desired orientation.

According to an embodiment, the auxiliary circuit is realized in/on a layer of flexible material that is laminated over the planar support.

Sensing devices adapted to be bonded on the electric board of this disclosure for building sensing systems according to the present disclosure, are galvanically isolated and supplied through antennas for contactless power supplying, such as, for example, the devices disclosed in the documents US 2009/0033467 and/or WO 2012/084295.

According to an embodiment, a sensing system of internal pressure along three coordinate axis of a block of building material, comprises an electric circuit board of this disclosure and sensing devices having galvanically isolated pressure sensors, each having a passivated sensing surface adapted to be placed in contact with the building material.

Further disclosed is a block of building material comprising a sensing system of internal pressure buried therein in which the building material is in direct contact with the sensitive passivated surfaces of the pressure sensors.

DETAILED DESCRIPTION OF THE PREFERRED EMBODIMENTS

Figure 1:
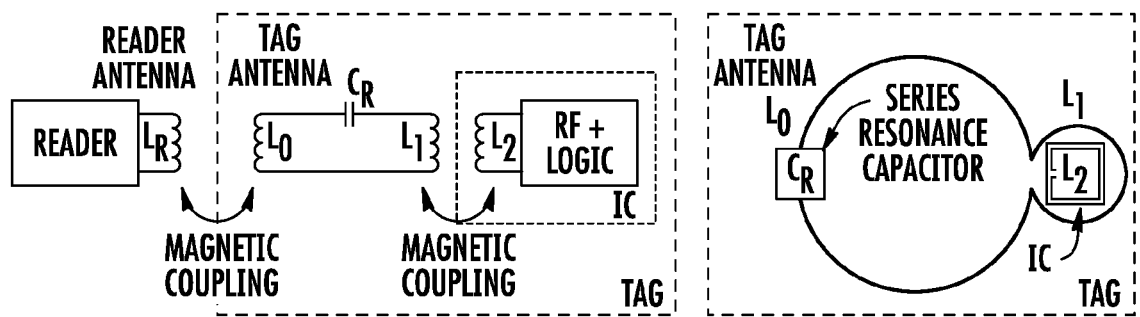
FIGS. 1 and 2 show known sensing devices, disclosed in US patent publication No. 2009/0033467, including circuits adapted to transmit in contactless fashion the electromagnetic energy for powering a buried sensor as in the prior art.
Figure 2:
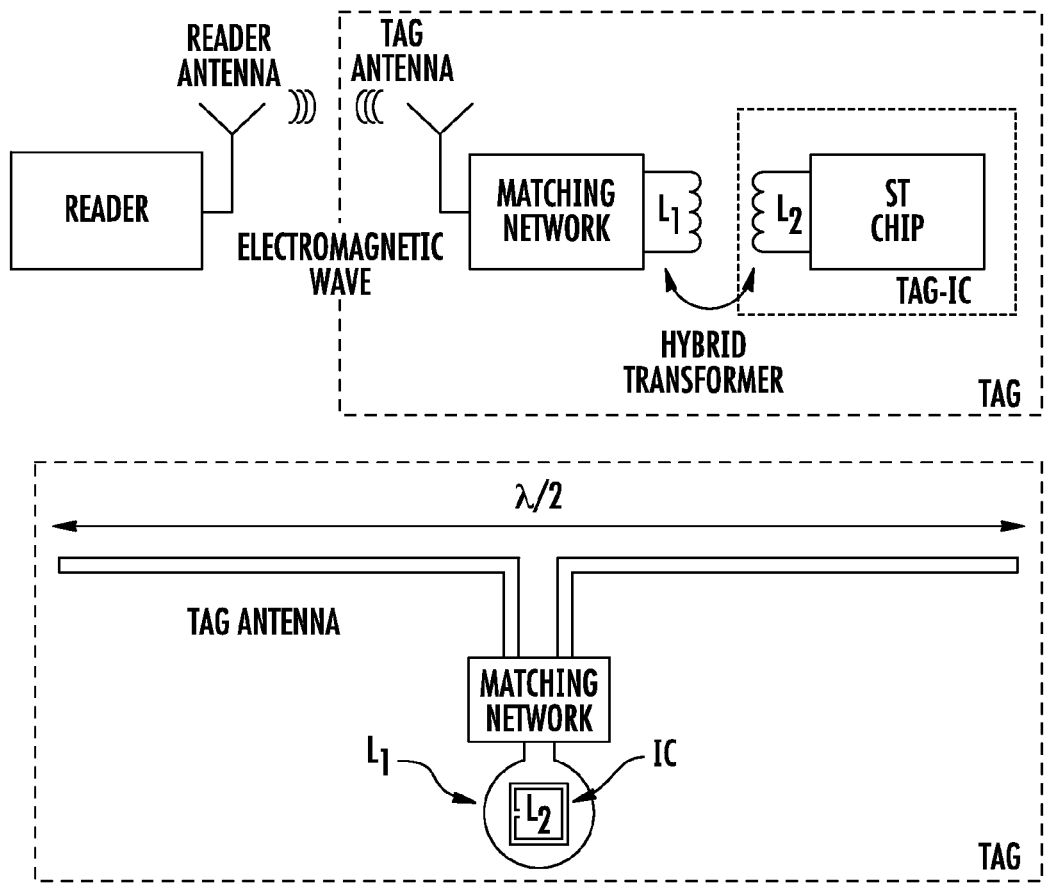
Figure 3:
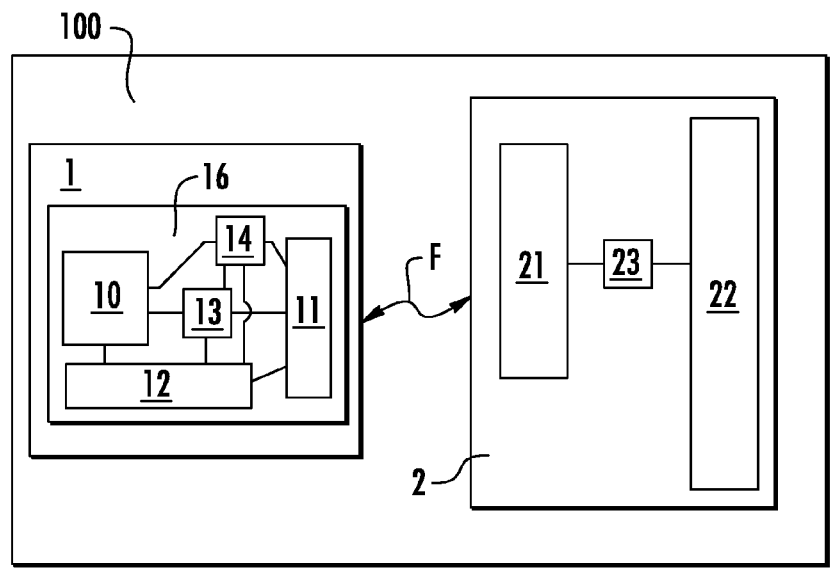
FIGS. 3 and 4 show known sensing devices, disclosed in WO 2012/084295, including circuits adapted to transmit in contactless fashion electromagnetic energy and information as in the prior art.
Figure 4:
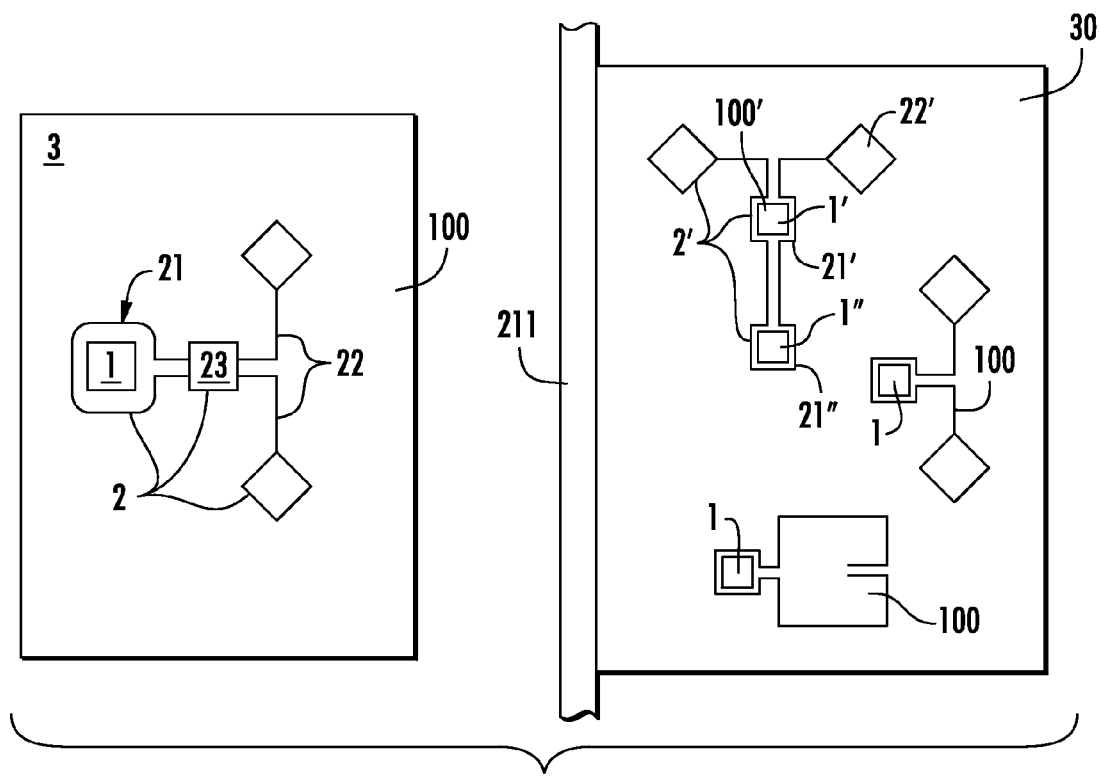
Figure 5:
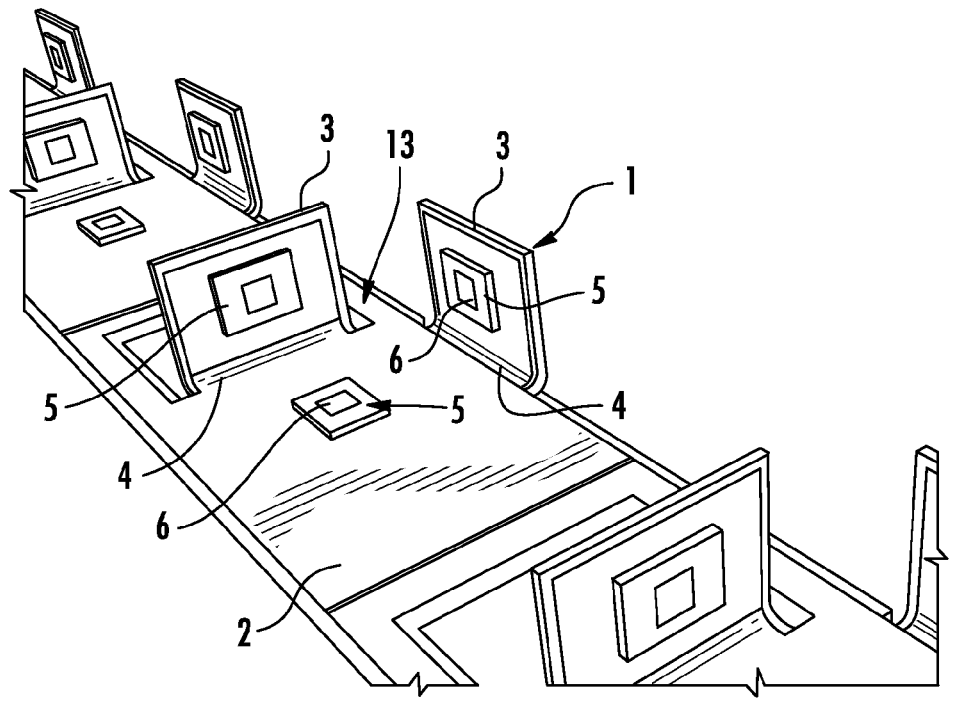
FIG. 5 shows an example of sensing system according to this disclosure having a support in the form of ribbon with folded wings, on which sensing devices that include pressure sensors are fixed.

An embodiment of the sensing system of pressure components in a block of building material along three coordinate axis is shown in FIG. 5. It comprises a support 1 that defines a base surface 2 and wings 3 confining with the base surface 2 along folding lines 4. On the base surface 2 and on the wings 3 there are sensing devices 5, each containing an integrated circuit IC, for example, of the type disclosed in WO 2012/084295, having respective pressure sensors 6 equipped with a planar sensing surface substantially coplanar with the plane defined by the wing 3 or coplanar with the base surface 2 on which they are installed.

Figure 6:
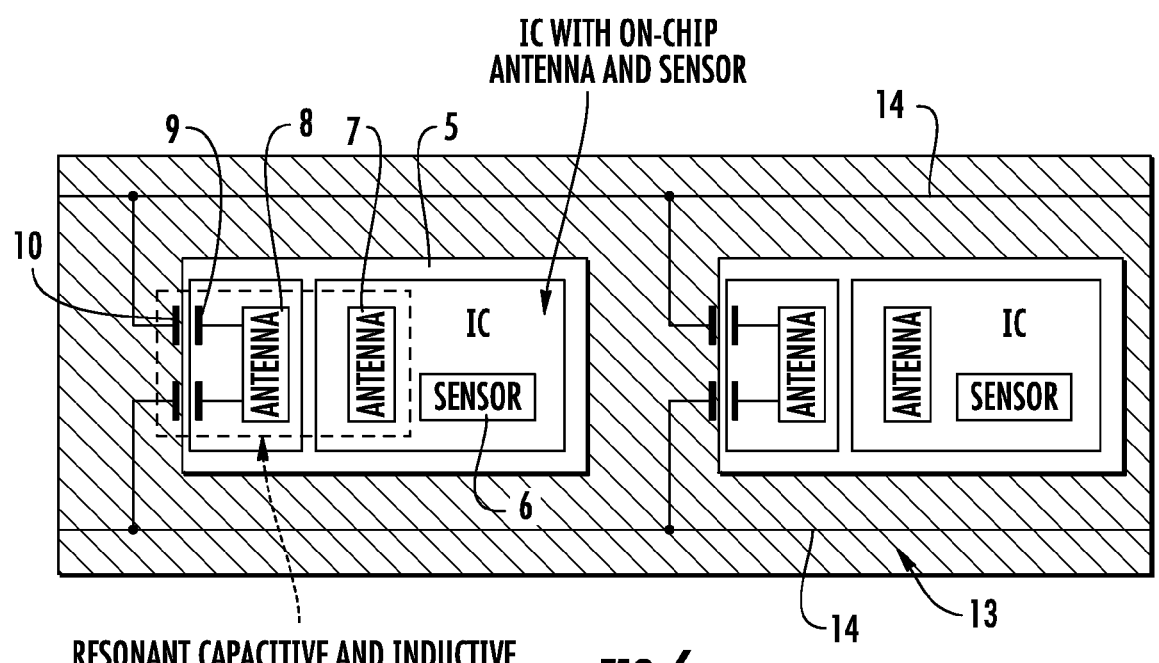
FIG. 6 is a detailed view of an electric board according to the present disclosure with sensing devices bonded on respective wings of a support and coupled in a contactless manner with electric communication lines.

The sensing devices 5 are powered and transmit/receive data through contactless electromagnetic coupling with electric communication lines 14, shown in FIG. 6, according to the disclosure of US 2009/0033467 and/or WO 2012/084295 and schematically sketched in figures from 1 to 4.

This kind of contactless power supplying and transceiving is particularly convenient because the sensing devices 5 and the integrated circuits IC contained in the sensing devices 5 are galvanically isolated from the electric communication lines 14, and this increases their reliability and thus the reliability of the whole system. Moreover, the sensing devices 5 may be fixed, for example, by bonding, after heaving realized the electric circuit board comprising the support 1 and the auxiliary circuit provided by the electric communication lines 14 and by the capacitive coupling plates destined to be electromagnetically coupled with respective plates of the sensing devices 5.

Once the sensing devices 5 are mounted, the wings 3 are folded, eventually hot folded if the material used for the support 1 does not allow a cold folding, up to assuming the desired orientation.

The sensing system according to this disclosure may be fabricated by realizing an electric circuit board by forming the plane support 1 to make it have at least one base surface 2 and at least two foldable wings 3 along folding lines 4, thus realizing the auxiliary circuit with the electric communication lines 14 and the electromagnetic expansion antennas thereon. Then the sensing devices 5 are fixed on the electric board to be galvanically isolated from the electric communication lines 14 and to be electromagnetically coupled with them for transmitting/receiving data and to be powered in a contactless fashion. Finally, the wings 3 are folded along folding lines.

The planar support 1, having at least a base surface 2 and at least two foldable wings 3, the auxiliary circuit containing the electric communication lines 14 and the capacitive coupling plates 10 which galvanically isolate sensing devices that will be electromagnetically coupled in a contactless fashion to the electric communication lines 14, provides a planar electric board with foldable wings that may be realized separately from the sensing devices. This electric circuit board may also be used in sectors different from the monitoring of structures of building material, for supplying and keeping oriented directional sensors of any type. More generally, it could be used for realizing sensing systems of components along three coordinate axis of any physical vector characteristic, obtained by bonding on the electric board sensing devices having directional sensors of this physical amount or characteristic.

For example, with a planar electric board according to the present disclosure, it is possible to realize sensing systems of the direction of electromagnetic waves by bonding on its base surface 2 and on its wings 3 sensing devices, embedding directional sensors of electromagnetic waves, galvanically isolated and electromagnetically coupled with the electric connection lines 14, thus folding the wings 3 to orient the directional sensors of electromagnetic waves according to orthogonal planes in respect to a triplet of coordinate axis. The sensing devices 5 will be powered in a contactless fashion by electromagnetic coupling to the electric communication lines 14, for example, according to the techniques disclosed in US 2009/0033467 and/or WO 2012/084295. The signals generated by the sensors will be transmitted on the electric communication lines 14.

An advantage of the planar electric circuit board with foldable wings of this disclosure is that it may be fabricated at a relatively small cost. Indeed, it is possible to realize on the support 1, the electric connection lines 14 and the electromagnetic expansion antennas for forming the circuits shown in FIGS. 6 and 7a through planar processes. For example, these circuits may be realized directly on the support 1 with the technology used for fabricating a PCB (Printed Circuit Board), or by electro-plating or ink-jet, or also by laminating on the support 1 with a process Roll-to-Roll (R2R) a layer 13 on which or in which the electric connection lines 14 are defined along with the electromagnetic expansion antennas 19, of the type illustrated in US 2009/0033467 and/or WO 2012/084295, destined to be electromagnetically coupled to respective antennas for contactless power supplying 8 of the sensing devices 5.

Figure 7A:
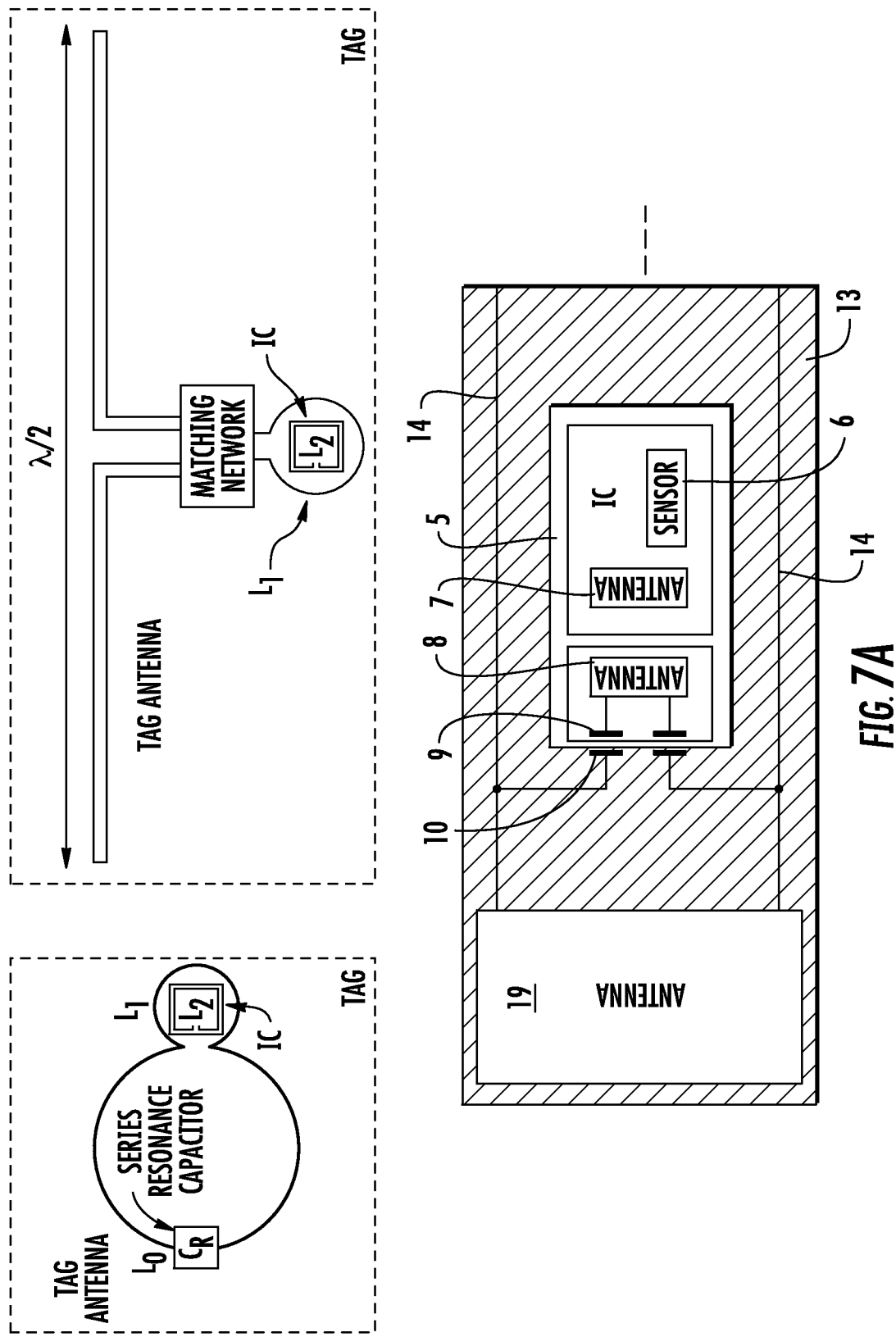
FIG. 7a is an embodiment of the electric board of FIG. 6 with a transceiving and contactless power supplying antenna connected to the electric communication lines.
Figure 7B:
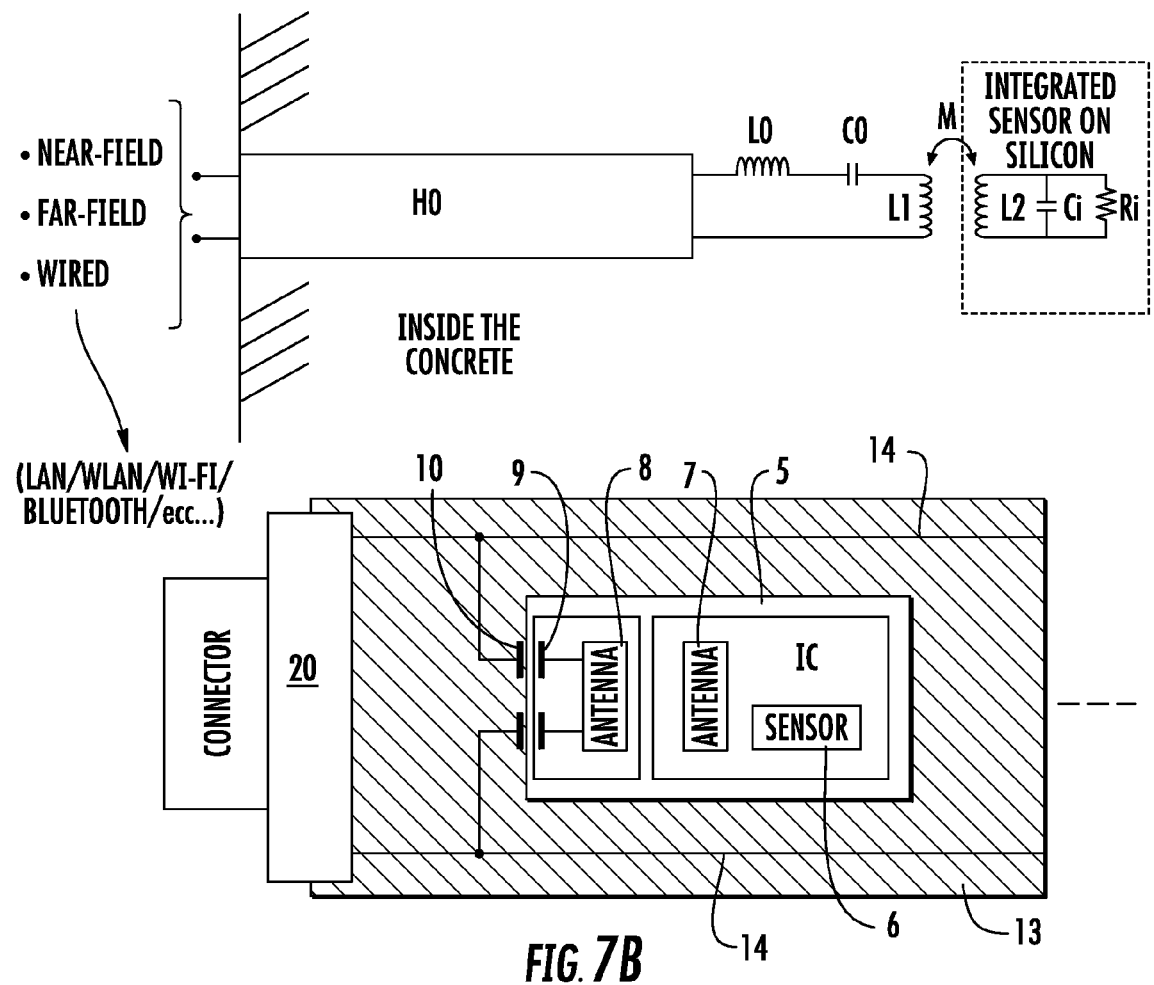
FIG. 7b is an embodiment of the electric circuit board of FIG. 6 wherein the electric communication lines are connected to the outside through a cable and through related connection terminals.

By connecting to a common electric line all the capacitive coupling plates 10 of the support, sketched in FIGS. 6, 7a and 7b as plates 10 of capacitors placed in front of respective capacitive coupling plates 9 embedded in the package of the sensing device 5, it is possible to irradiate simultaneously a variable electromagnetic field on all the antennas 7 for contactless power supplying of the integrated circuits IC embedding the sensors 6 through the antennas 8 embedded in the package.

As shown in FIGS. 7a and 7b, the electric communication lines 14 will transmit the signals coming from the sensors through a single antenna 19 embedded in the auxiliary circuit or through connection terminals CONNECTOR of electric connections 20.

In the embodiment of FIG. 5, the support 1 is substantially a ribbon with numerous wings 3 folded perpendicularly thereto. This support may be obtained by realizing the planar ribbon depicted in FIG. 8a, engraved to define the wings 3 foldable along folding lines 4. In any case the particular embodiment of the support 1 is non-limiting.

Figure 8A:
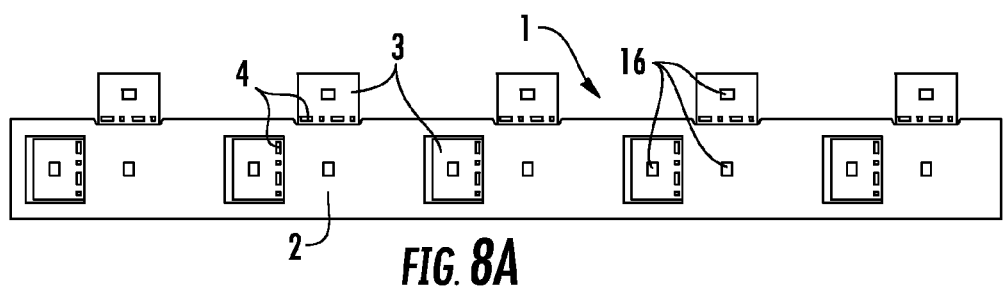
FIGS. 8a and 8b are plant views of embodiments of the support according to this disclosure with wings not yet folded and spaces destined to house sensing devices.

In the embodiment shown in FIG. 8a, particularly useful for realizing sensing systems of internal forces of a block made of building material, the support 1 is provided with holes 16 realized on the wings 3 and on the base surface 2 in correspondence of the places in which the sensing devices 5 will be fixed. The function of these holes 16 is to allow the building material to come into direct contact, when poured, with the sensitive surface of the sensor 6 embedded in the sensing device 5. In this particular application, sensing devices 5 embedding the integrated circuits IC disclosed in WO 2012/084295, that include passivated sensitive surfaces that may be placed in contact with the building material, will be conveniently used.

From the above considerations, it is clear that the support 1 of the electric board with foldable wings of this disclosure may also have no hole 16. In the above cited example of the sensing system of the direction of arrival of electromagnetic waves, these holes 16 may be omitted and the wings 3 and the base surfaces 2 may be solid.

Even in the case of pressure sensors 6, it is possible to omit these holes 16, in order to reduce the pressure measured by the sensor itself and to increase, in this way, the greatest pressure value that the sensor may sense.

Figure 8B:
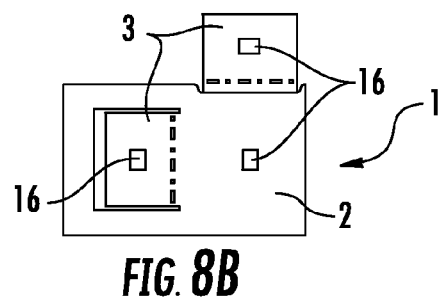

According to another embodiment depicted in FIG. 8b, the support 1 comprises only two rectangular wings 3 confining with the rectangular base surface 2 along consecutive sides thereof. This embodiment may be embedded in blocks of building materials having relatively reduced sizes.

The support 1 may be made of a material resistant at environmental temperature and easily hot workable such as Teflon, or a thermoplastic material, or LCP (Liquid-crystal polymers), or polyimide or yet FR4, ROGER, BT.

For ease of explanation, hereinafter reference will be made to the case shown in FIG. 8a in which the planar electric circuit board of this disclosure is destined to the realization of systems for sensing internal forces in a block of building material. It is clear that what will be stated holds, mutatis mutandis, also when the electric board does not have holes 16 because it is destined to other objectives, such as, for example, for realizing systems for sensing the direction of arrival of electromagnetic waves.

Embodiments of integrated circuits IC of the sensing devices 5 adapted to be fixed to the electric board of this disclosure for realizing the cited sensing systems to be buried in blocks of building material for monitoring building structures of large size, are shown, for example, in US 2009/0033467 and/or WO 2012/084295.

Figure 9:
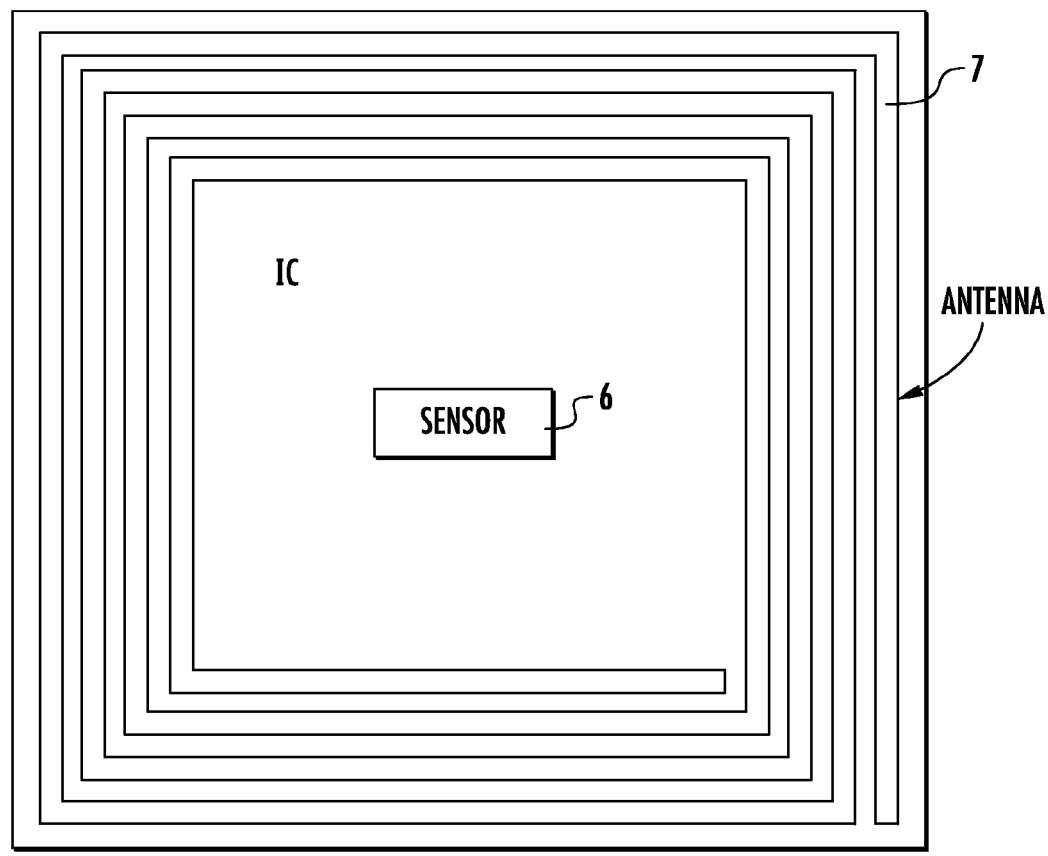
FIG. 9 illustrates an embodiment of a sensing device having a pressure sensor and a respective antenna for contactless power supplying and for transceiving data.
Figure 10:
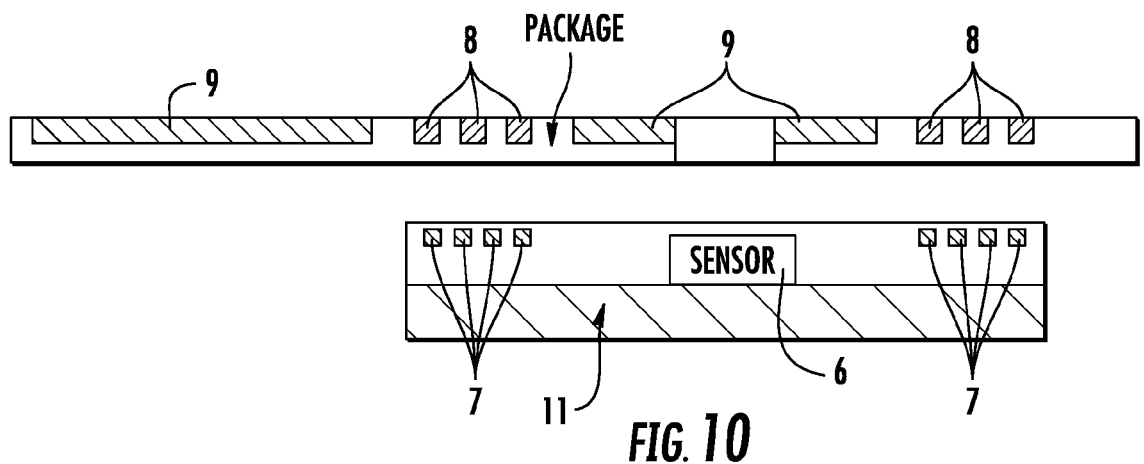
FIG. 10 is a cross sectional view of the sensing device of FIG. 9 and of an embodiment of a package substrate embedding an antenna electromagnetically coupled to the antenna of the sensing device, and metallization for realizing a capacitive coupling with electric communication lines on the support according to the present disclosure.

More generally, these integrated circuits IC and the related sensing devices 5 that embed them, that are galvanically isolated, will be of the type shown in FIGS. 9 and 10, respectively. They have a sensor 6, that may be a pressure sensor 6, and an antenna 7 for contactless power supply to the sensor 6 realized on a substrate 11, for example, of a semiconducting material. As shown in FIG. 9, conveniently the antenna 7 will be coupled to an electromagnetic expansion antenna 8, electrically connected to other capacitive coupling plates 9, embedded in the package of the sensing device, and destined to be electromagnetically coupled to respective capacitive coupling plates 10 defined in the auxiliary circuit, shown in FIGS. 6, 7A and 7B, of the planar electric board of this disclosure. With this capacitive coupling between the plates 9 and 10, it is possible to prevent soldering that may be damaged when subjected to the high pressures that typically are generated in a block of building material, and as a consequence this may lead to a malfunctioning of at least one sensing device 5.

Figure 11A:
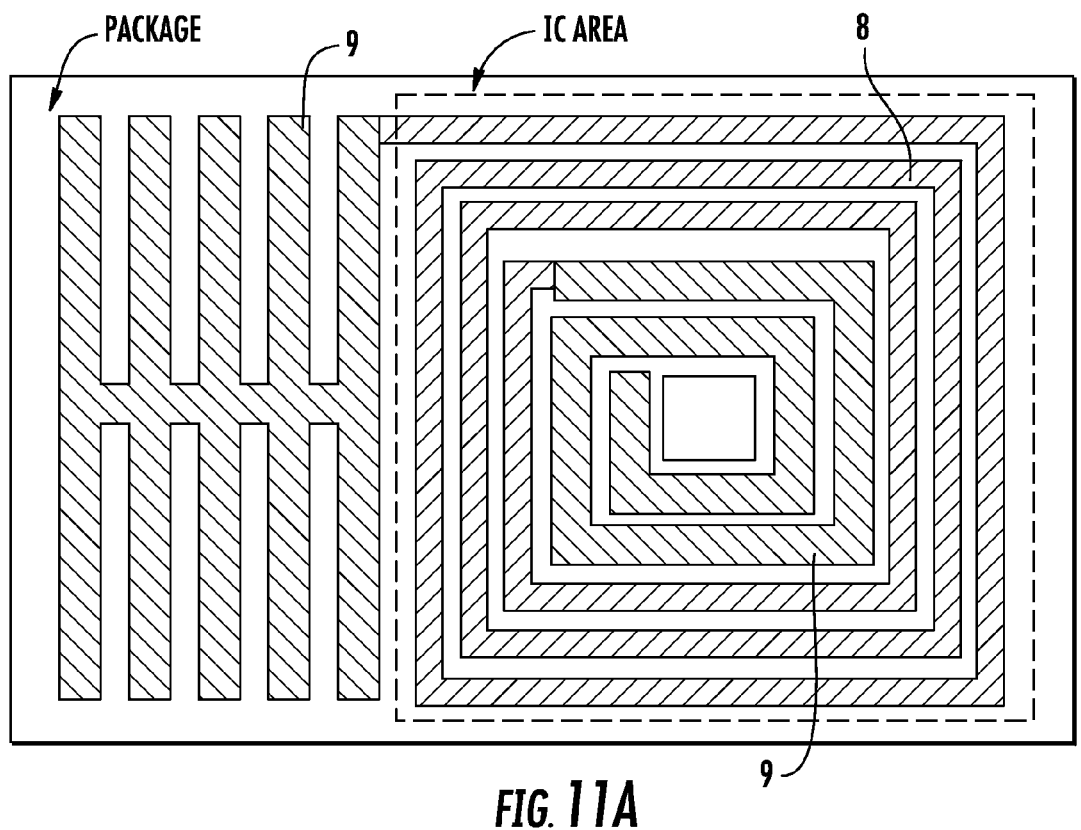
FIGS. 11A and 11B are plan views of embodiments of the package substrate shown in FIG. 10.
Figure 11B:
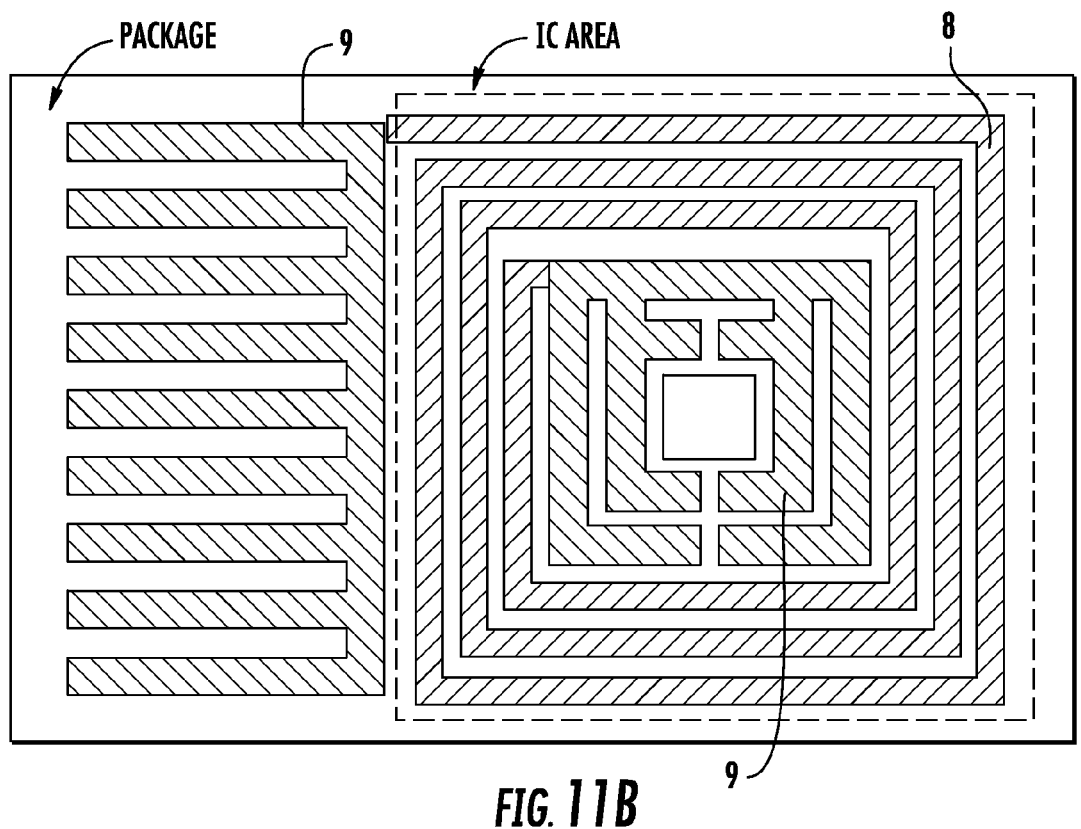

Exemplary patterns of capacitive coupling plates 9 embedded in the package of a sensing device 5 usable in the sensing system of this disclosure, are shown in FIGS. 11A and 11B. Preferably, the plates 9 are defined according to geometries adapted to minimize losses for eddy currents. In the shown embodiments, the sensitive surface of sensor 6 is not covered by the package to allow the building material to pour through the package and be in direct contact with the sensor.

Figure 12:
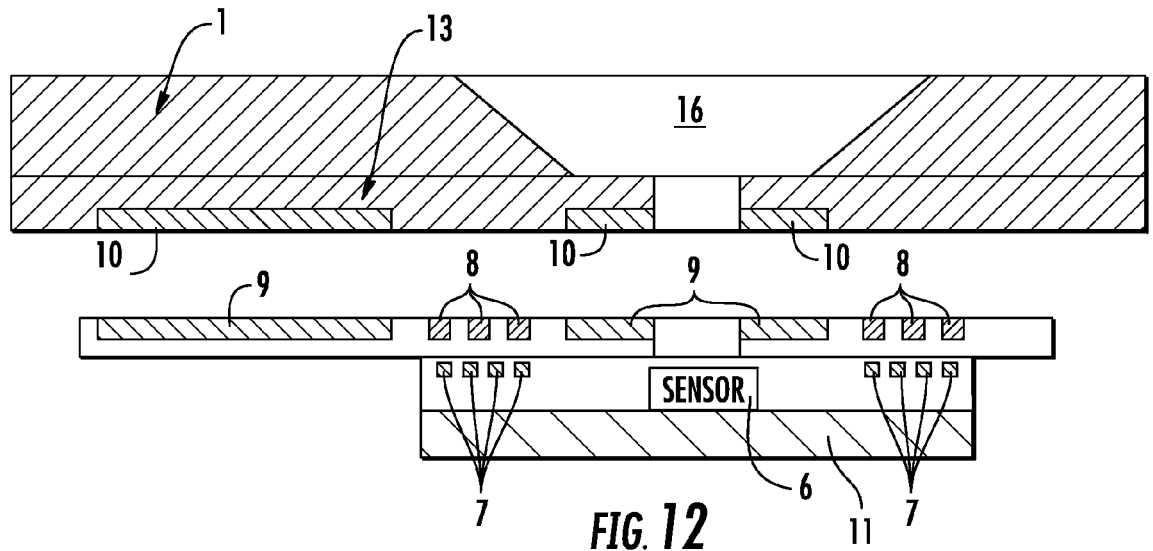
FIG. 12 is a cross section of the sensing device and of the related substrate of FIG. 10, and of the support on which the electric communication lines are defined.

FIG. 12 is a sectional view of a portion of the planar electric board of this disclosure and of the sensing device of FIG. 10. It shows the support 1 with the hole 16, in order to make a building material (for example concrete) come into contact with the sensitive surface of the sensor 6, and the layer 13 on which there is the auxiliary circuit. In the embodiment of FIG. 12 only the capacitive coupling plates 10 of the auxiliary circuit are shown, electromagnetically coupled to the respective plates 9 of the sensing device 5, that remains galvanically isolated from the planar electric board.

Figure 13:
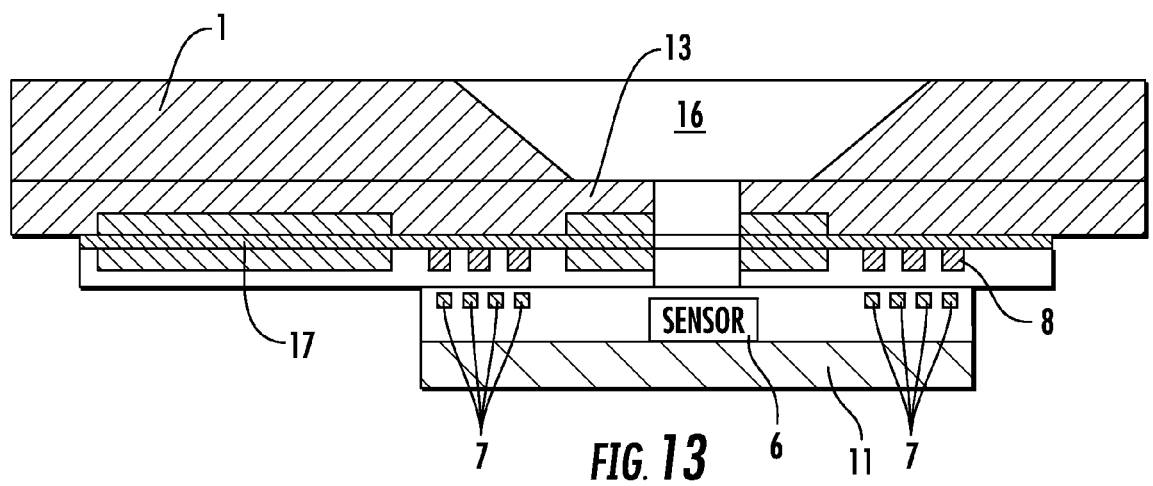
FIG. 13 illustrates the sensing device of FIG. 10 with the related substrate fixed to a layer of flexible material with electromagnetic expansion antennas and with capacitive coupling plates.

The sensing device 5 will be fixed to the layer of flexible material 13 by bonding or through a layer of silicon oxide or of dielectric 17, as shown in FIG. 13.

Figure 14:
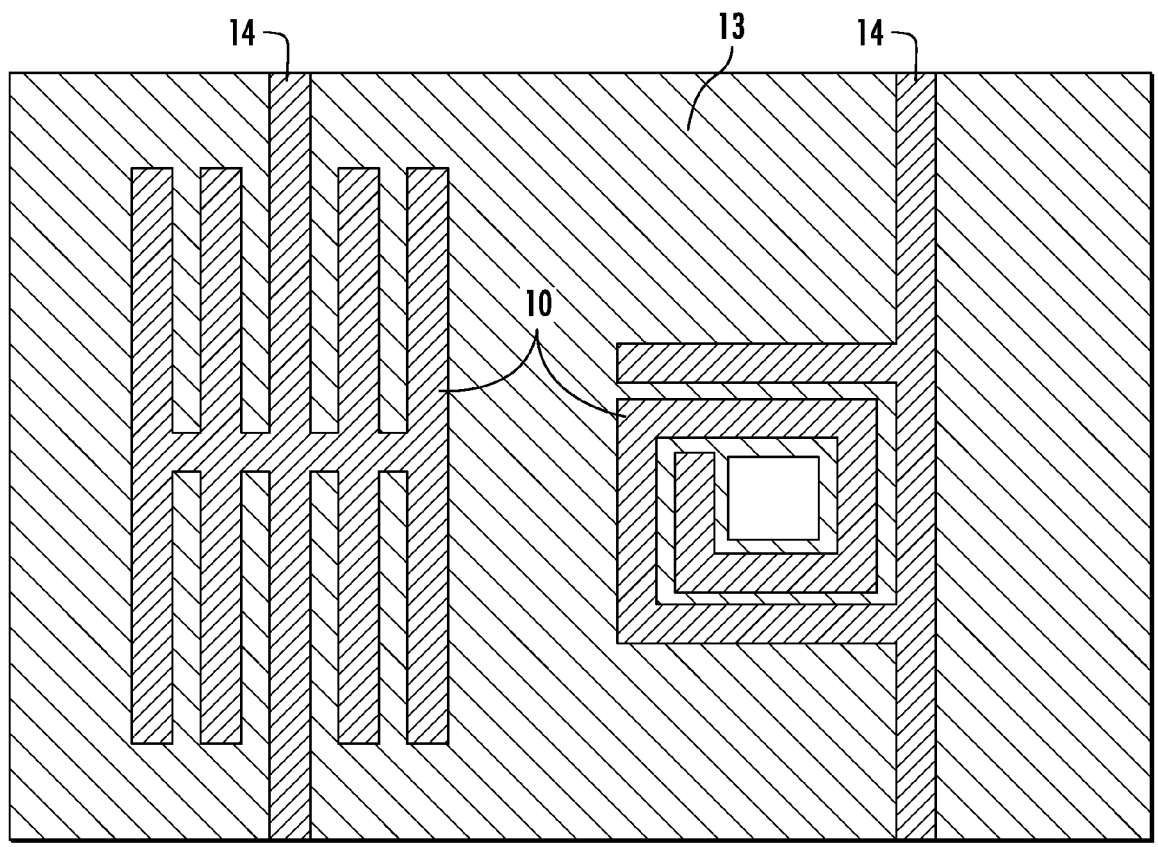
FIG. 14 is a top view of a layer of flexible material with capacitive coupling plates of a support according to an embodiment of this disclosure.
Figure 16:
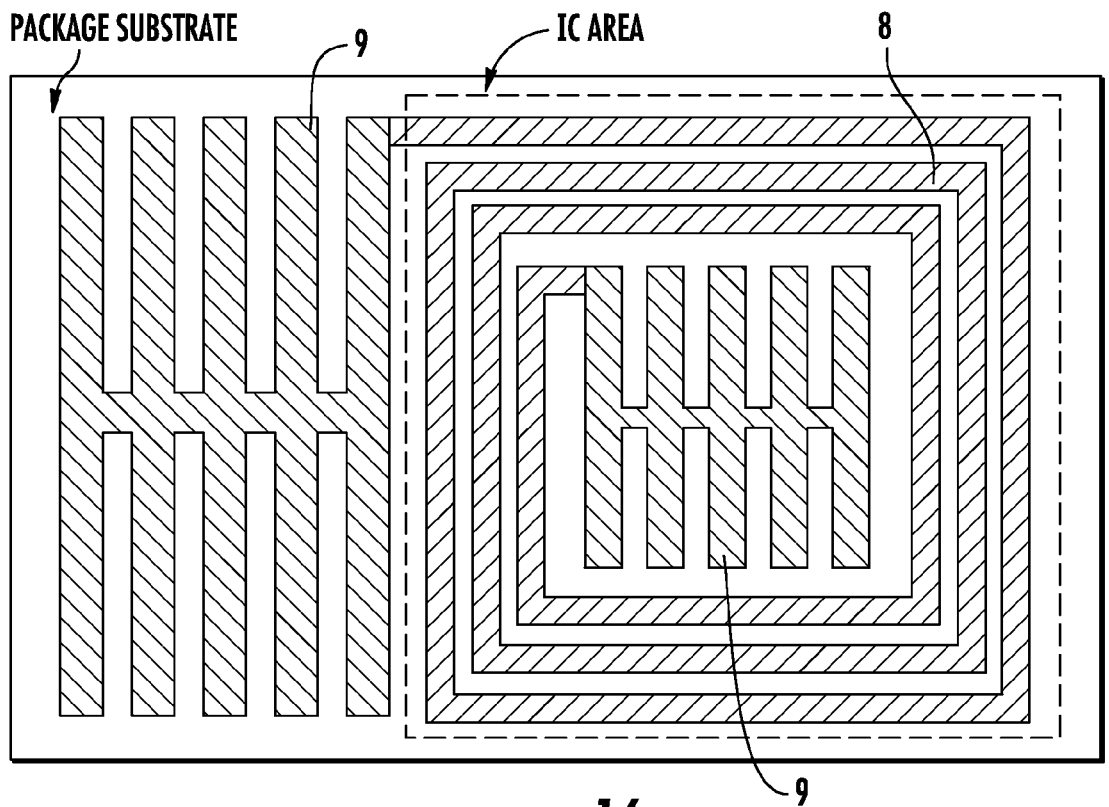
FIG. 16 is a top view of a layer of a package according to an embodiment of this disclosure.

As stated above making reference to FIG. 6, the auxiliary circuit will be defined on a layer 13, that may be of flexible material laminated onto the support 1, embedding capacitive coupling plates 10 connected to a common electric line 14. These plates 10 may be realized, for example, as shown in FIGS. 14 and 16, connected to respective electric connection lines 14 to which all plates 10 are connected in parallel. As a consequence the system is fault tolerant, meaning that if at least one sensing device 5 is damaged, the other sensing devices will continue to function normally.

Preferably, the plates 10 in the layer 13 will have a shape corresponding to that of plates 10 embedded in the package of the sensing device, to obtain a good electromagnetic coupling.

Figure 15:
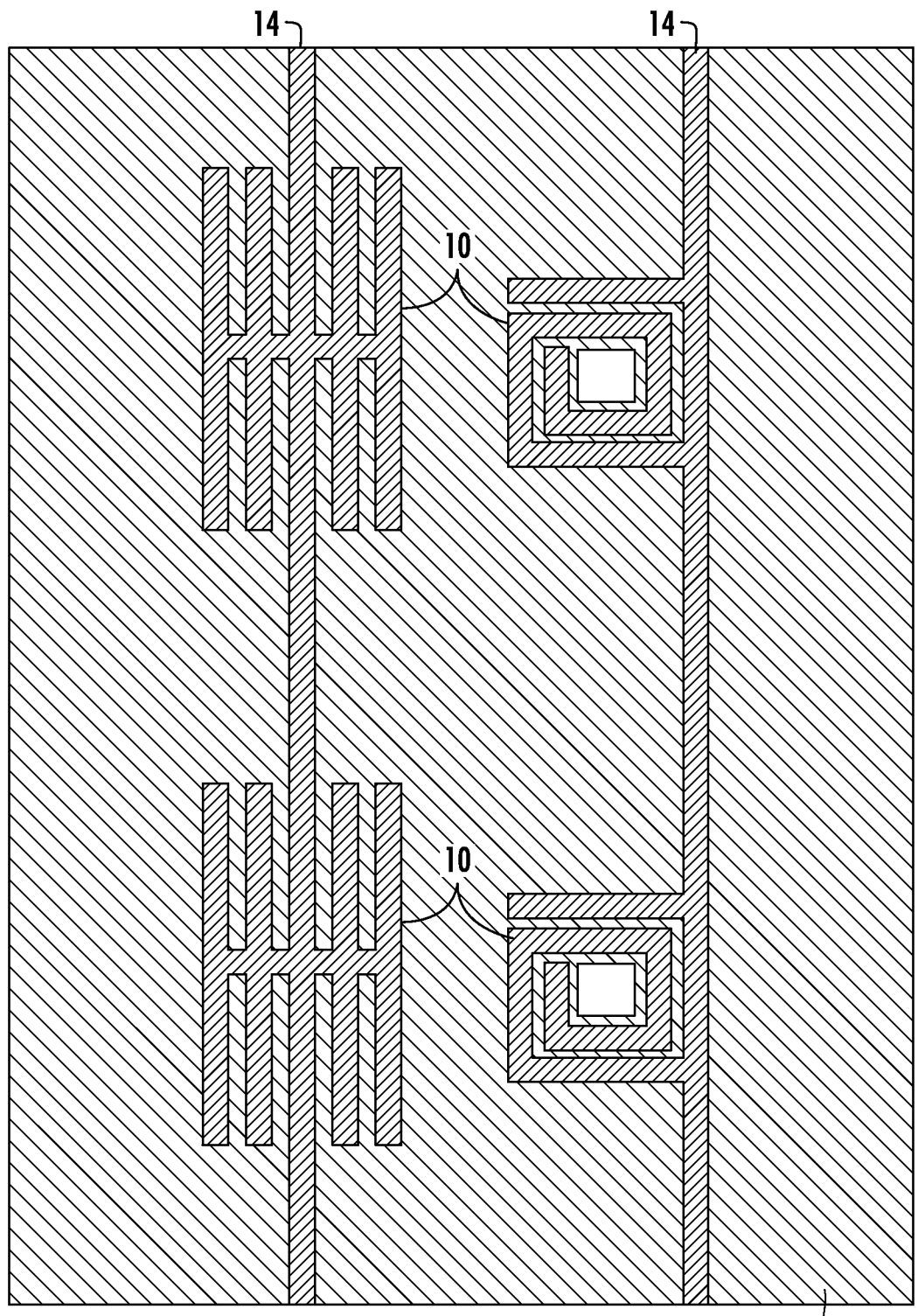
FIG. 15 shows capacitive coupling plates of the layer of flexible material of FIG. 14 connected among them.
Figure 17:
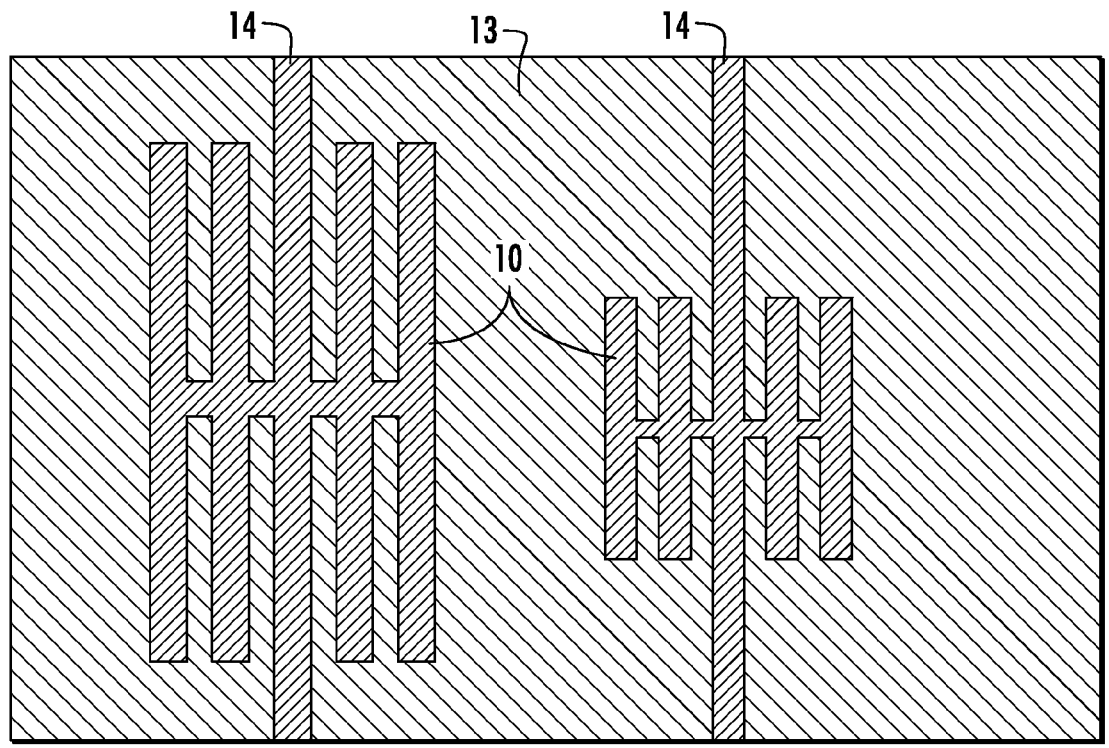
FIG. 17 is a top view of a layer of flexible material with capacitive coupling plates of a support according to an embodiment of this disclosure.
Figure 18:
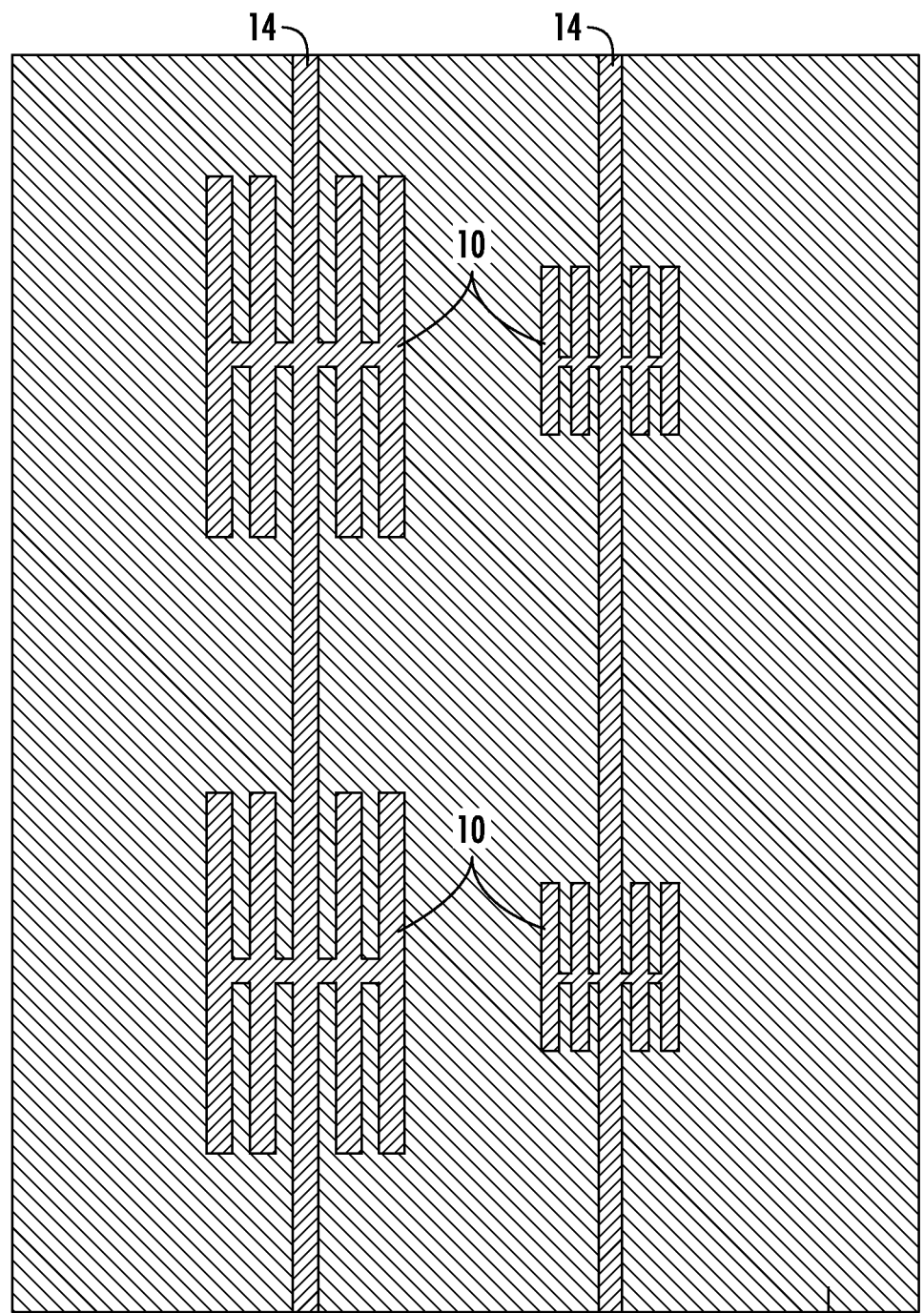
FIG. 18 shows capacitive coupling plates connected among them through electric communication lines of the layer of flexible material of FIG. 17.

The capacitive coupling plates 9 and 10 may have a different shape, as shown in FIGS. 16, 17 and 18, that are similar to FIGS. 11A, 14 and 15. It is to be noticed that the package of FIG. 16, differently from that of FIGS. 11A and 11B, does not have any hole for exposing the sensor of the sensing device, that remains covered. Similarly, the layer 13 shown in FIGS. 17 and 18 of the planar electric board has no hole.

Figure 19:
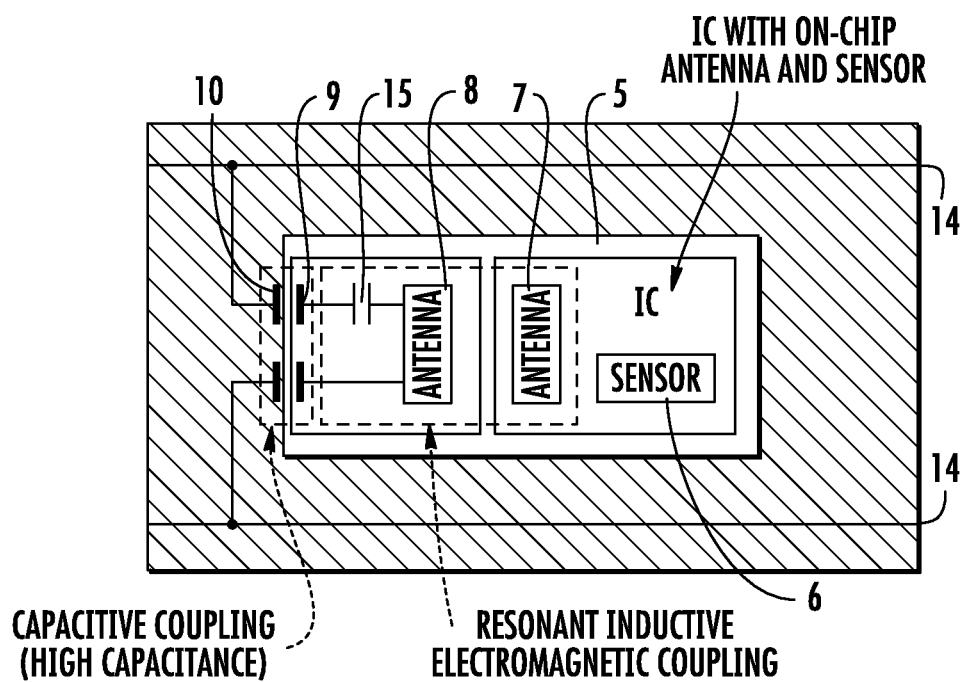
FIG. 19 is a detailed view of a structure according to the present disclosure and shows a substrate of a sensing device in which there are auxiliary metals that provide an auxiliary capacitance in series with the electromagnetic expansion antennas.
Figure 20:
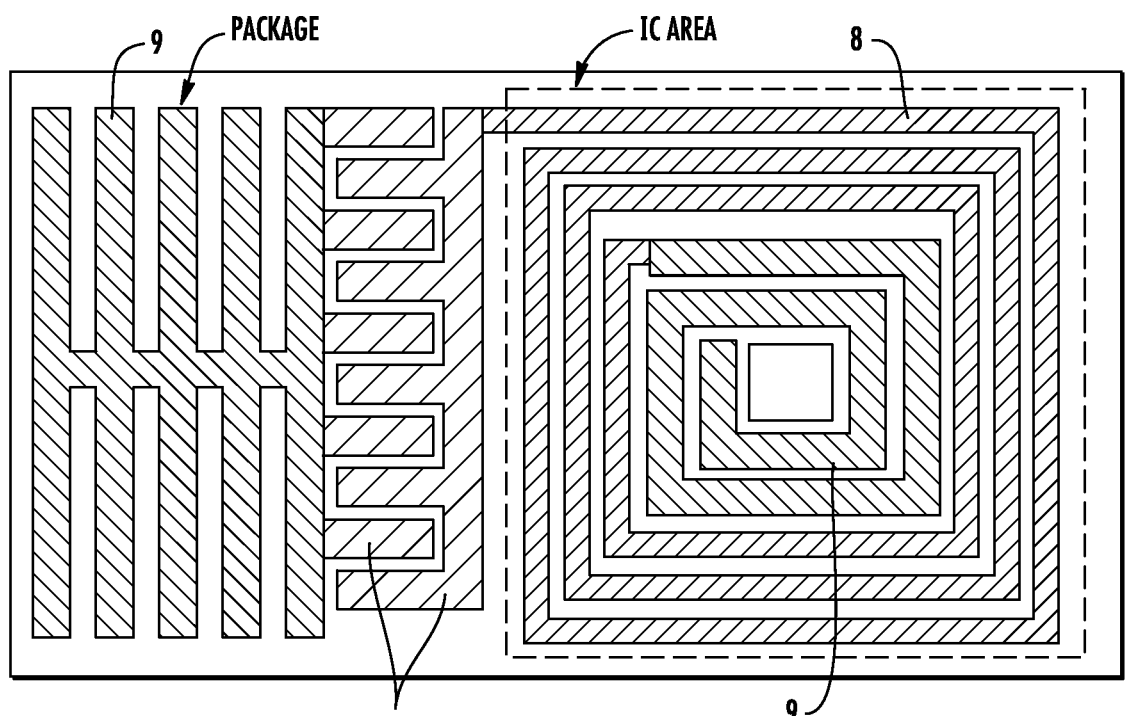
FIG. 20 is a plan view of an embodiment of the package substrate with auxiliary metals providing the auxiliary capacitance depicted in FIG. 19.

In order to regulate the resonance frequency of the connection between the electromagnetic expansion antenna 8 and the capacitive coupling plate 9 embedded in the package of the sensing devices 5, it is possible to interpose therebetween a capacitance 15, shown in FIGS. 19 and 20, for example, by defining a metal layer 15 with interdigitated portions separated by a dielectric.

Figure 21:
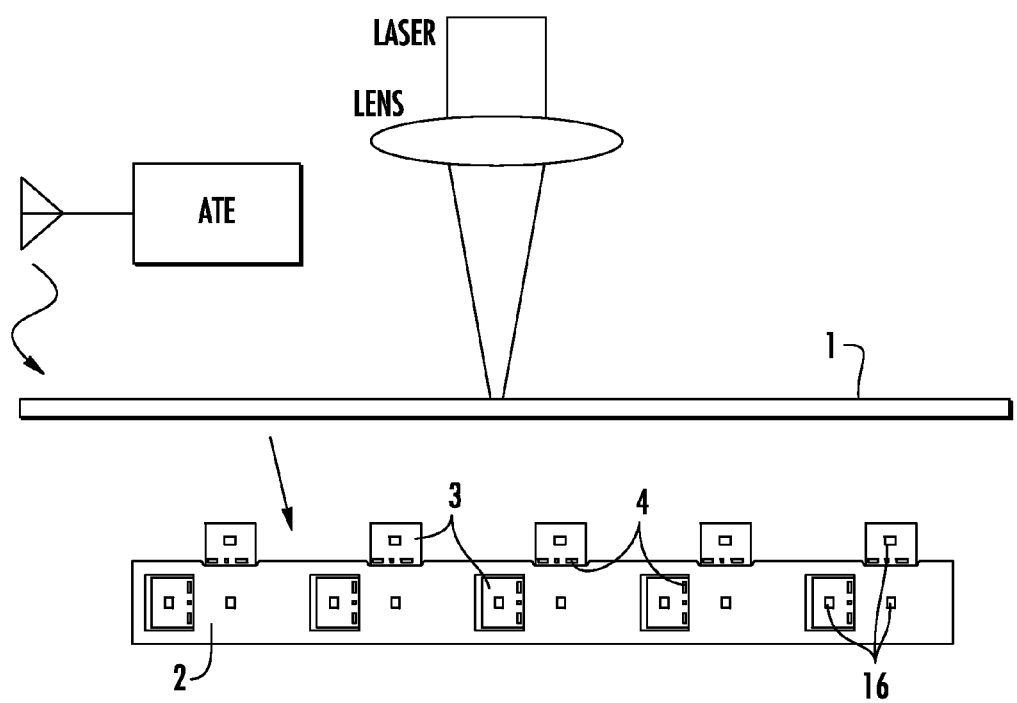
FIG. 21 illustrates schematically how to perform a contactless test and a trimming of the structure according to the present disclosure.
Figure 22:
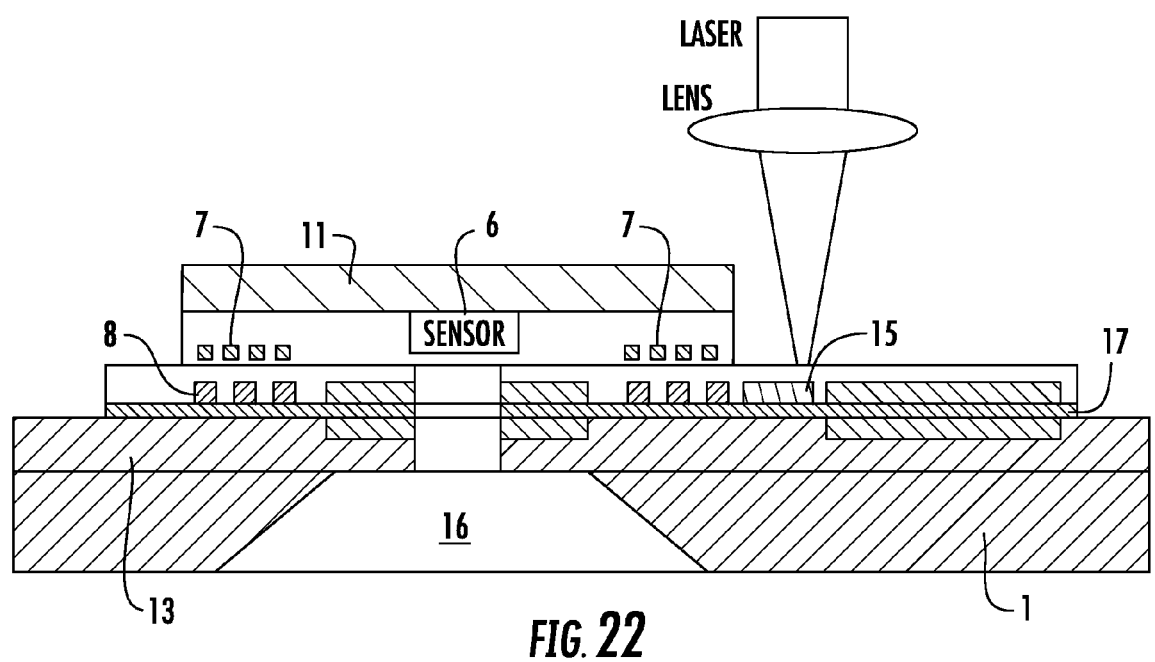
FIGS. 22 and 23 illustrate schematically how to trim the auxiliary metallization of FIG. 20.
Figure 23:
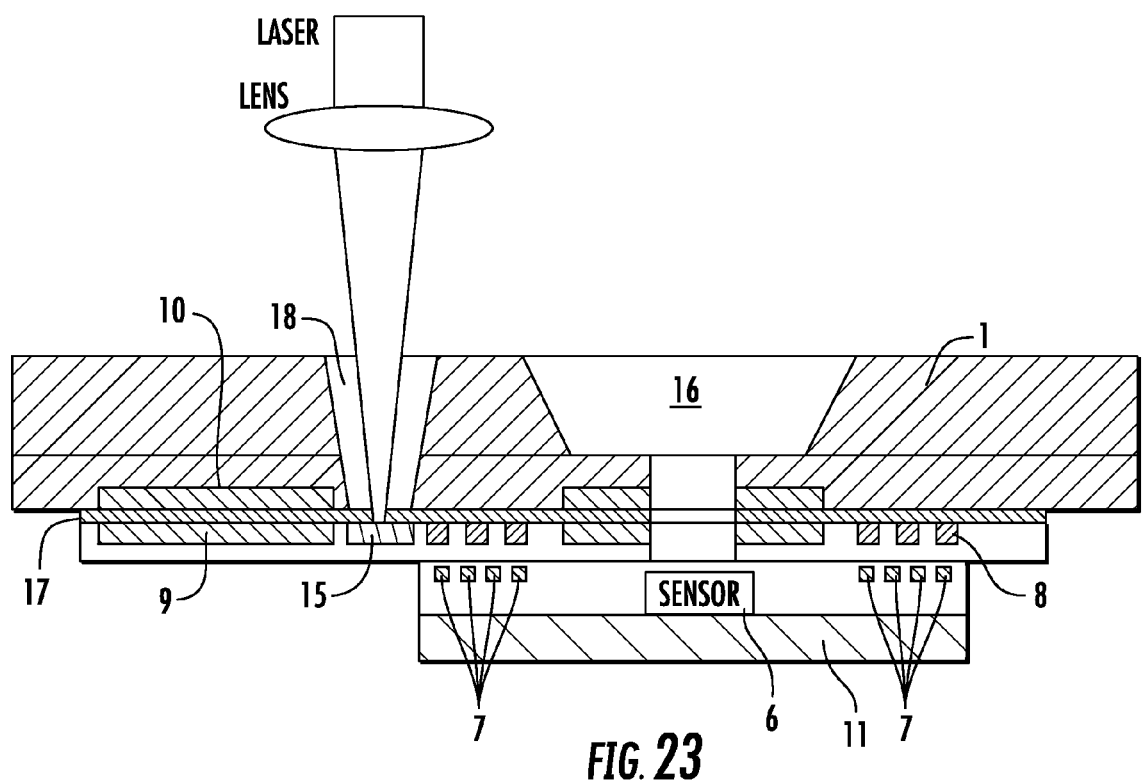

After having fixed the sensing devices 5 on the electric board and before having folded the wings 3, the sensing system of this disclosure is still substantially planar, thus it may be easily fully or partially tested with a contactless technique using an ATE (Automatic Test Equipment), as shown in FIG. 21, to which an antenna may be connected that may be of Hertzian type, or of magnetic or capacitive type. Before folding the wings, the sensing system is planar thus, if the used sensing devices 5 are the ones disclosed referring to FIGS. 19 and 20, using a laser (FIGS. 22 and 23) it is possible to carry out a trimming or fine tuning of the resonance frequencies of at least a part of the system. This may be done, for example, by acting on capacitors 15 by properly modifying the corresponding metallization embedded in the package of the sensing device 5. This operation may be executed by acting from the side of the sensing device (FIG. 22) or from the side of the support 1 (FIG. 23). In the latter case, the support 1 and the eventual layer 13 that embeds the auxiliary circuit, will have holes 18 such to expose the metallization 15 also after the sensing device 5 has been fixed to the electric board.

Figure 24:
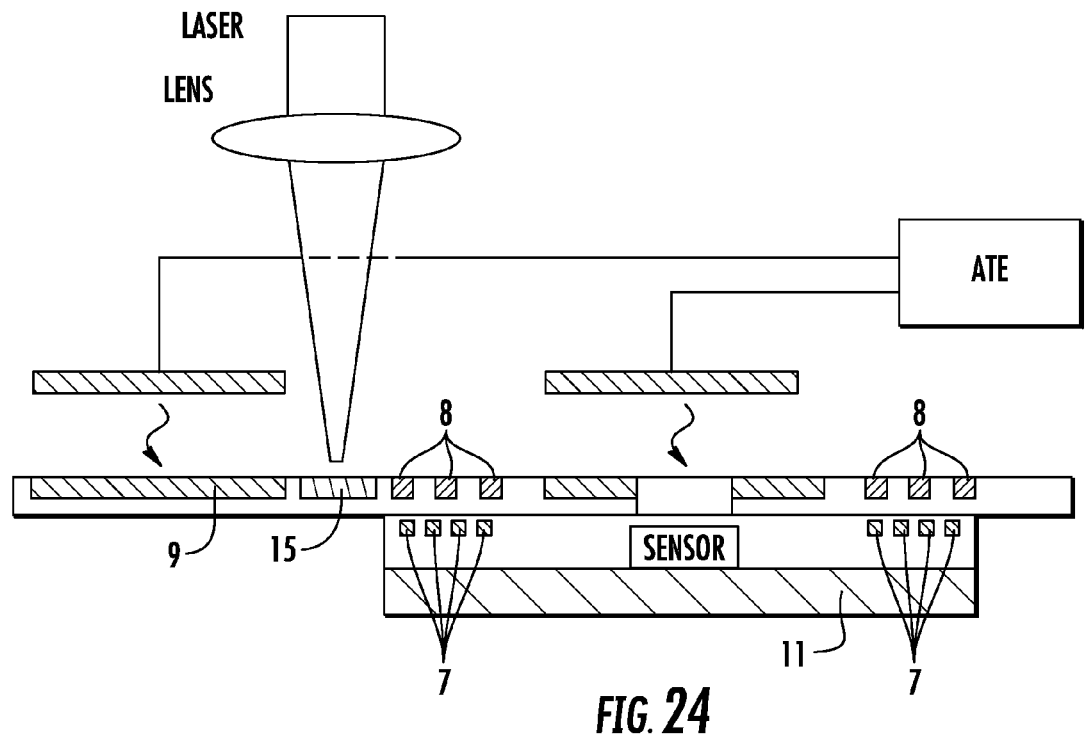
FIG. 24 illustrates schematically how to perform a contactless test and a trimming of a sensing device mounted on the respective substrate.

As an alternative, as shown in FIG. 24, it is even possible to test only the sensing devices through an ATE capacitively coupled therewith, and to carry out the above mentioned trimming of the metallization 15 before mounting the devices on the electric board.

That which is claimed is:

1. A planar electric circuit board comprising:
   a planar support comprising a foldable material defining a base surface and a plurality of wings coupled to the base surface along respective folding lines so that the plurality of wings, when folded along the folding lines, are erected with respect to the base surface and remain in that position, the plurality of wings being folded along the respective folding lines to be oriented along planes orthogonal to each other and to the base surface; and
   an auxiliary circuit on the planar support comprising pairs of capacitive coupling plates defined on the plurality of wings and on the base surface, and a plurality of electric communication lines coupled to corresponding ones of the pairs of capacitive coupling plates.

2. The planar electric circuit board according to claim 1 wherein the foldable material comprises a hot foldable material.

3. The planar electric circuit board according to claim 1 wherein the foldable material comprises a cold foldable material.

4. The planar electric circuit board according to claim 1 further comprising a common antenna coupled to the plurality of electric communication lines and configured for transceiving data and for contactless power supplying.

5. The planar electric circuit board according to claim 1 further comprising a plurality of terminals coupled to corresponding ones of the plurality of electric communication lines coupled to corresponding ones of the plurality of terminals for transceiving data and for power supplying.

6. The planar electric circuit board according to claim 1 further comprising a layer of flexible material configured to carry the auxiliary circuit and being secured onto the planar support.

7. The planar electric circuit board according to claim 1 wherein the auxiliary circuit comprises conductive traces on the planar support.

8. The planar electric circuit board according to claim 1 wherein the planar support has holes on the wings and the base surface for positions onto which galvanically isolated devices are to be fixed.

9. The planar electric circuit board according to claim 1 wherein the planar support comprises at least one of Teflon, polyimide, liquid crystal polymers, thermoplastic materials; and wherein the planar support is engraved to define the folding lines.

10. A sensing system comprising:
    a planar support comprising a foldable material defining a base surface and a plurality of wings coupled to the base surface along respective folding lines so that the plurality of wings, when folded along the folding lines, are erected with respect to the base surface and remain in that position;
    an auxiliary circuit on the planar support comprising pairs of capacitive coupling plates defined on the plurality of wings and on the base surface, and a plurality of electric communication lines coupled to corresponding ones of the pairs of capacitive coupling plates; and a plurality of sensing devices comprising a respective directional sensor and at least one antenna coupled thereto and configured for contactless power supplying and data transceiving, the plurality of sensing devices being positioned on the planar support so that the at least one antenna is coupled to a respective one of the capacitive coupling plates.

11. The sensing system according to claim 10 wherein the plurality of wings are folded along respective folding lines to be oriented along planes orthogonal to each other and to the base surface.

12. The sensing system according to claim 10 wherein the plurality of sensing devices are coupled to the planar support by bonding.

13. The sensing system according to claim 10 wherein the plurality of sensing devices comprises galvanically isolated pressure sensors, each having a passivated sensing surface adapted to be in direct contact with a building material.

14. The sensing system according to claim 10 wherein the plurality of sensing devices comprises directional sensors of electromagnetic waves, each configured for sensing the intensity of a component of an electromagnetic wave orthogonal to a sensing surface of the sensor.

15. A sensing system comprising:
a support comprising a foldable material defining a base surface and a plurality of wings coupled to the base surface along respective folding lines so that the plurality of wings, when folded along the folding lines, are erected with respect to the base surface and remain in that position, the plurality of wings being folded along the respective folding lines to be oriented along planes orthogonal to each other and to the base surface; and
a plurality of sensing devices, each carried by a respective one of the plurality of wings.

16. The sensing system according to claim 15 wherein the plurality of sensing devices each comprises a respective directional sensor and at least one antenna coupled thereto and configured for contactless power supplying and data transceiving.

17. The sensing system according to claim 16 further comprising a plurality of capacitive coupling plates carried by the support; and wherein each sensing device is carried the support so that the at least one antenna is coupled to a respective one of the capacitive coupling plates.

18. The sensing system according to claim 15 wherein the support comprises at least one of Teflon, polyimide, liquid crystal polymers, thermoplastic materials; and wherein the support is engraved to define the folding lines.

19. A method of making a sensing system comprising:
folding, along folding lines, a support comprising a foldable material defining a base surface and a plurality of wings coupled to the base surface along respective folding lines so that the plurality of wings are erected with respect to the base surface and remain in that position, the plurality of wings being folded along the respective folding lines to be oriented along planes orthogonal to each other and to the base surface; and
mounting each of a plurality of sensing devices to a respective one of the plurality of wings.

20. The method according to claim 19 wherein the plurality of sensing devices each comprises a respective directional sensor and at least one antenna coupled thereto and configured for contactless power supplying and data transceiving.

21. The method according to claim 20 further comprising coupling a plurality of capacitive coupling plates to be carried by the support; and wherein mounting each sensing device comprises mounting each so that the at least one antenna is coupled to a respective one of the capacitive coupling plates.

22. A sensing system comprising:
a support comprising a foldable material defining a base surface and a plurality of wings coupled to the base surface along respective folding lines so that the plurality of wings, when folded along the folding lines, are erected with respect to the base surface and remain in that position;
a plurality of sensing devices, each carried by a respective one of the plurality of wings and comprising a respective directional sensor and at least one antenna coupled thereto and configured for contactless power supplying and data transceiving; and
a plurality of capacitive coupling plates carried by said support, each sensing device being carried by the support so that the at least one antenna is coupled to a respective one of the capacitive coupling plates.

23. A method of making a sensing system comprising:
folding, along folding lines, a support comprising a foldable material defining a base surface and a plurality of wings coupled to the base surface along respective folding lines so that the plurality of wings are erected with respect to the base surface and remain in that position; and
mounting each of a plurality of sensing devices to a respective one of the plurality of wings, each sensing device comprising a respective directional sensor and at least one antenna coupled thereto and configured for contactless power supplying and data transceiving; and
coupling a plurality of capacitive coupling plates to be carried by the support so that the at least one antenna is coupled to a respective one of the capacitive coupling plates.

* * * * *

UNITED STATES PATENT AND TRADEMARK OFFICE
CERTIFICATE OF CORRECTION

| | | |
|---|---|---|
| PATENT NO. | : 8,967,000 B2 | Page 1 of 1 |
| APPLICATION NO. | : 14/027990 | |
| DATED | : March 3, 2015 | |
| INVENTOR(S) | : Pagani et al. | |

It is certified that error appears in the above-identified patent and that said Letters Patent is hereby corrected as shown below:

In the Claims

Column 9, Line 45    Delete: "carried the"
                                  Insert: --carried by the--

Signed and Sealed this
Eighteenth Day of August, 2015

Michelle K. Lee
*Director of the United States Patent and Trademark Office*